(12) United States Patent
Kleinig et al.

(10) Patent No.: US 8,569,234 B2
(45) Date of Patent: Oct. 29, 2013

(54) COMPOSITIONS AND METHODS FOR INCLUDING MELANOGENESIS IN A SUBJECT

(75) Inventors: Michael John Kleinig, Brunswick (AU); Kenneth B. Kirby, Palm Beach Gardens, FL (US); Berno I. Pettersson, Jr., Perry, GA (US)

(73) Assignee: Clinuvel Pharmaceuticals Limited, Melbourne (AU)

( * ) Notice: Subject to any disclaimer, the term of this patent is extended or adjusted under 35 U.S.C. 154(b) by 1299 days.

(21) Appl. No.: 11/664,879

(22) PCT Filed: Oct. 7, 2005

(86) PCT No.: PCT/AU2005/001552
§ 371 (c)(1),
(2), (4) Date: Feb. 9, 2011

(87) PCT Pub. No.: WO2006/037188
PCT Pub. Date: Apr. 13, 2006

(65) Prior Publication Data
US 2011/0263508 A1    Oct. 27, 2011

Related U.S. Application Data

(60) Provisional application No. 60/617,359, filed on Oct. 8, 2004.

(51) Int. Cl.
| | | |
|---|---|---|
| *A61K 38/08* | (2006.01) | |
| *A61K 38/10* | (2006.01) | |
| *A61K 38/12* | (2006.01) | |
| *A61K 38/34* | (2006.01) | |
| *C07K 14/68* | (2006.01) | |
| *C07K 5/12* | (2006.01) | |
| *C07K 7/00* | (2006.01) | |
| *C07K 7/06* | (2006.01) | |
| *C07K 7/08* | (2006.01) | |

(52) U.S. Cl.
USPC .......... 514/10.7; 514/18.6; 530/312; 530/317

(58) Field of Classification Search
None
See application file for complete search history.

(56) References Cited

U.S. PATENT DOCUMENTS

| 4,866,038 | A | 9/1989 | Hruby et al. |
| 4,918,055 | A | 4/1990 | Hruby et al. |
| 5,049,547 | A | 9/1991 | Hruby et al. |
| 6,444,234 | B1 | 9/2002 | Kirby et al. |
| 6,787,152 | B2 | 9/2004 | Kirby et al. |

FOREIGN PATENT DOCUMENTS

| AU | 70828/87 A | 8/1987 |
| WO | WO 02/080878 | * 10/2002 |

OTHER PUBLICATIONS

Defintion of analog from http://cancerweb.ncl.ac.uk/omd/about.html, pp. 1-5. Accessed Jul. 7, 2005.*
WO 02/080878 Machine translation of specification. 2002.*
WO 02/080878 Machine translation of claims. 2002.*
Dawson B. V. et al., The Journal of Investigative Dermatology, vol. 94, No. 4 (Apr. 1990) pp. 432-435.
Schwartzmann-Solon A.M. et al., Brazilian Journal of Medical and Biological Research, vol. 31, No. 12 (1998), pp. 1557-1564.
Dorr R. T. et al., Investigational New Drugs, vol. 6, No. 4 (Dec. 1998), pp. 251-258.

* cited by examiner

*Primary Examiner* — Julie Ha
(74) *Attorney, Agent, or Firm* — Birch, Stewart, Kolasch & Birch, LLP.

(57) ABSTRACT

Described herein are compositions comprising an alpha-MSH analogue and a transdermal delivery system and methods for inducing melanogenesis and/or preventing UV radiation-induced skin damage in a subject by topical administration of these compositions.

6 Claims, 6 Drawing Sheets

COMPOSITIONS AND METHODS FOR INCLUDING MELANOGENESIS IN A SUBJECT

This National Phase application claims priority under 35 U.S.C. 119(e) to U.S. Provisional Application No. 60/617,359 filed on Oct. 8, 2004. The entire contents of these applications are herein fully incorporated by reference.

BACKGROUND

The melanocortins include a family of peptide hormones that induce pigmentation by interaction with melanocortin-1 receptors (MC1R) in the epidermis.[1] The primary pigmentary hormone that is released from the pars intermedia of the pituitary gland in some non-human animals, and from UV exposed keratinocytes in human skin, is alpha melanocyte stimulating hormone (alpha-MSH).[1] This 13 amino acid peptide binds to MC1R to induce cyclic AMP-mediated signal transduction, which leads to the synthesis of melanin polymers from DOPA precursors.[1] Two types of melanins can be expressed in humans. The brownish-black pigment eumelanin is believed to convey protection from sun damage, whereas the reddish, sulfur-containing pigment, pheomelanin, is often expressed in light-skinned human populations that report a poor tanning response to sunlight.[2] These poorly-tanning, easily-burning populations often possess defects in the MC gene[3] and are generally thought to be at a greater risk of developing both melanoma and non-melanoma skin cancers.[4,5]

It has previously been disclosed that a super-potent derivative of alpha-MSH, MELANOTAN (Nle$^4$-D-Phe$^7$-alpha MSH, also referred to herein as "MELANOTAN-1" or "MT1"), can induce tanning in human volunteers.[6] MELANOTAN ([Nle$^4$, D-Phe$^7$]-alpha-MSH) contains two amino acid substitutions and is approximately 100 to 1,000-fold more potent than the native hormone at inducing pigmentation in experimental systems such as the frog skin bioassay or in cultured human keratinocytes.[7] In humans, MELANOTAN ([Nle$^4$, D-Phe$^7$]-alpha-MSH) primarly induces eumelanin synthesis in the skin in concert with its tanning effect.[8] Although melanotropins have been postulated to affect immunologic changes,[9,10,11] all of the prior trials reported only minimal side effects such as facial flushing and transient GI upset, unless doses greater than those needed for tanning were administered.[12]

There is compelling evidence that melanotropic peptides may provide a potential for increasing melanin pigmentation of human skin. Synthetic MSH may be used to enhance skin pigmentation of normal or light-skinned individuals to protect them from the hazards of solar radiation. Several studies have suggested that individuals whose skin tends to burn easily on exposure to the sun and does not tan readily are at higher risk of both nonmelanoma skin tumors and of cutaneous melanoma.[16,17,18] There is unambiguous evidence that UV radiation is responsible for skin cancer in humans. In the face of increased deterioration of the ozone layer and the increasing incidence of and mortality from skin cancer, the ability to stimulate the skin's own "protective mechanism" of tanning may prove extremely important as photoprotective strategy.

Accordingly, described herein are compositions and methods for inducing melanogenesis in a human subject by topically administering alpha-MSH analogues to the subject which surprisingly leads to increased melanin density levels in the subject. By increasing melanin levels in a subject, it is possible to reduce or prevent the occurrence of UV radiation-induced skin damage in the subject.

SUMMARY

Described herein are compositions and methods for inducing melanogenesis in a subject. The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below. Like numbers or letters represent the same elements throughout the figures.

DETAILED DESCRIPTION

Before the present compounds, compositions, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

Throughout this specification and in the claims, unless the context requires otherwise, the word "comprise," or variations such as "comprises" or "comprising," will be understood to imply the inclusion of a stated integer or step or group of integers or steps but not the exclusion of any other integer or step or group of integers or steps.

It must be noted that, as used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

"Optional" or "optionally" means that the subsequently described event or circumstance can or cannot occur, and that the description includes instances where the event or circumstance occurs and instances where it does not.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

References in the specification and in the claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

By "prevent" or "preventing" means the administration of a composition to a subject or a system at risk for an undesirable condition. The condition can include a disease or a predisposition to a disease. Prevention can range from a reduction in the severity of the condition to the complete ablation of the condition.

By "effective amount and time" means a therapeutic amount and time needed to achieve the desired result or results, e.g., inducing melanogenesis in a subject.

By "induce" means initiating a desired response or result that was not present prior to the induction step. The term "induce" also includes the term "potentiate."

The term "potentiate" means sustaining a desired response at the same level prior to the potentiating step or increasing the desired response over a period of time.

The term "melanogenesis" as referred to herein is defined as the ability of a subject to produce melanins by melanin-producing cells, or melanocytes.

The term "homologous desensitization" as referred to herein is defined as the inhibition of a cellular response upon continuous exposure to an agonist.

The term "epidermal tissue" as referred to herein includes in particular the skin of a subject.

The term "transdermal" as used herein encompasses the administration of the compounds that go into the skin or go through the skin using formulations such as, but not limited to, topical formulations, buccal patches, skin patches, or transdermal patches.

The term "topical" as used herein encompasses administration by applying conventional topical preparations such as lotions, sprays, creams, gels, or solutions for localized percutaneous delivery and/or by solution for systemic and/or localized delivery to epidermal tissue of the subject.

The term "subject" as referred to herein includes in particular a mammal, most particularly a human.

Disclosed are compounds, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a number of different alpha-MSH analogues and transdermal delivery systems are disclosed and discussed, each and every combination and permutation of the alpha-MSH analogue and transdermal delivery system are specifically contemplated unless specifically indicated to the contrary. This concept applies to all aspects of this disclosure including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Described herein are compositions and methods for inducing melanogenesis in a human subject. The compositions and methods herein increase melanin production without inducing homologous desensitization of the melanocortin-1-receptors of the subject. This is accomplished by administering alpha-MSH analogues to the subject so that low concentrations of the alpha-MSH analogue are present in the plasma of the subject. In general, higher doses of alpha-MSH analogue are required to increase melanin production in a subject. However, undesirable side effects can occur when high doses of alpha-MSH analogue are administered. By increasing melanin production in a subject, it is possible to prevent the occurrence of UV radiation-induced skin damage in a subject that would normally be susceptible to such damage.

In one aspect, the present invention provides a composition for topical administration to induce melanogenesis in a subject, or to prevent UV radiation-induced skin damage in a subject, which comprises:

(i) a transdermal delivery system (TDS); and
(ii) an alpha-MSH analogue.

In another aspect, the present invention also provides a method for inducing melanogenesis in a subject, or for preventing UV radiation-induced skin damage in a subject, which comprises topically administering to the subject a composition which comprises:

(i) a transdermal delivery system (TDS); and
(ii) an alpha-MSH analogue.

Preferably, the composition is administered to provide the alpha-MSH analogue in an effective amount and time to induce melanogenesis by the melanocytes in epidermal tissue of the subject without inducing homologous desensitization of the melanocortin-1 receptor of the subject.

Preferably also, the composition is administered to provide an effective amount of said alpha-MSH analogue to induce melanogenesis by the melanocytes in epidermal tissue of the subject, wherein the alpha-MSH analogue is administered at a level not exceeding 10 μg/ml in the plasma of the subject for a period of at least 4 hours.

In yet another aspect, the present invention extends to the use of a composition which comprises:

(i) a transdermal delivery system (TDS); and
(ii) an alpha-MSH analogue.

in the manufacture of a topical preparation for inducing melanogenesis in a subject, or for preventing UV radiation-induced skin damage in a subject.

Preferably, the subject is a human subject.

The term "alpha-MSH analogue" referred to herein is defined as a derivative of alpha-MSH which exhibits agonist activity for the melanocortin-1 receptor (MC1R), the receptor to which alpha-MSH binds to initiate the production of melanin within a melanocyte. Such derivatives include derivatives in which (i) one or more amino acid residues are deleted from the native alpha-MSH molecule at the N-terminal end, the C-terminal end, or both; and/or (ii) one or more amino acid residues of the native alpha-MSH molecule are replaced by another natural, non-natural or synthetic amino acid residue; and/or (iii) an intramolecular interaction forms as a cyclic derivative.

The use of any alpha-MSH analogue is contemplated in the compositions and methods described herein. Several derivatives of α-MSH have been synthesized.[19] The alpha-MSH analogues described in U.S. Pat. Nos. 4,457,864, 4,485,039, 4,866,038, 4,918,055, 5,049,547, 5,674,839 and 5,714,576 and Australian Patents Nos. 597630 and 618733, which are herein incorporated by reference for their teachings with respect to alpha-MSH analogues and the synthesis thereof, can be used in the compositions and methods described herein.

In one aspect, the alpha-MSH analogue may be a compound as disclosed in Australian Patent No. 597630, selected from:
(a) compounds of the formula:

Ac-Ser-Tyr-Ser-M-Gln-His-D-Phe-Arg-Trp-Gly-Lys-Pro-Val-NH$_2$

The alpha-MSH analogue may be a linear analogue as disclosed in U.S. Pat. No. 5,674,839, selected from the group consisting of:

Ac-Ser-Tyr-Ser-Nle-Glu-His-D-Phe-Arg-Trp-Lys-Gly-Pro-Val-NH$_2$
Ac-Ser-Tyr-Ser-Nle-Asp-His-D-Phe-Arg-Trp-Lys-Gly-Pro-Val-NH$_2$
Ac-Nle-Glu-His-D-Phe-Arg-Trp-Lys-Gly-Pro-Val-NH$_2$
Ac-Nle-Asp-His-D-Phe-Arg-Trp-Lys-Gly-Pro-Val-NH$_2$
Ac-Nle-Asp-His-D-Phe-Arg-Trp-Gly-NH$_2$
Ac-Nle-Glu-His-D-Phe-Arg-Trp-Lys-NH$_2$
Ac-Nle-Asp-His-D-Phe-Arg-Trp-Lys-NH$_2$
Ac-Nle-Glu-His-D-Phe-Arg-Trp-Orn-NH$_2$
Ac-Nle-Asp-His-D-Phe-Arg-Trp-Orn-NH$_2$
Ac-Nle-Glu-His-D-Phe-Arg-Trp-Dab-NH$_2$
Ac-Nle-Asp-His-D-Phe-Arg-Trp-Dab-NH$_2$
Ac-Nle-Glu-His-D-Phe-Arg-Trp-Dpr-NH$_2$
Ac-Nle-Glu-His-Phe-Arg-Trp-Lys-NH$_2$
Ac-Nle-Asp-His-Phe-Arg-Trp-Lys-NH$_2$

The alpha-MSH analogue may also be a cyclic analogue as disclosed in U.S. Pat. No. 5,674,839, selected from the group consisting of:

Ac—Nle—Glu—His—D—Phe—Arg—Trp—Lys—Gly—Pro—Val—NH$_2$ (cyclized)
Ac—Nle—Glu—His—D—Phe—Arg—Trp—Lys—NH$_2$ (cyclized)
Ac—Nle—Asp—His—D—Phe—Arg—Trp—Lys—NH$_2$ (cyclized)
Ac—Nle—Asp—His—D—Phe—Arg—Trp—Orn—NH$_2$ (cyclized)
Ac—Nle—Asp—His—D—Phe—Arg—Trp—Dab—NH$_2$ (cyclized)
Ac—Nle—Asp—His—D—Phe—Arg—Trp—Dpr—NH$_2$ (cyclized)
Ac—Ser—Tyr—Ser—Nle—Asp—His—D—Phe—Arg—Trp—Lys—Gly—Pro—Val—NH$_2$ (cyclized)
Ac—Ser—Tyr—Ser—Nle—Asp—His—D—Phe—Arg—Trp—Lys—NH$_2$ (cyclized)
Ac-Tyr-Ser-Nle-Asp-His-D-Phe-Arg-Trp-Lys-NH$_2$ (cyclized)
Ac—Ser—Nle—Asp—His—D—Phe—Arg—Trp—Lys—NH$_2$ (cyclized)
Ac—Nle—Asp—His—D—Phe—Arg—Trp—Lys—NH$_2$ (cyclized)
Ac—Nle—Asp—His—D—Phe—Arg—Trp—Lys—Gly—NH$_2$ (cyclized)
Ac-Nle-Asp-His-D-Phe-Arg-Trp-Lys-Gly-Pro-NH$_2$ (cyclized)
Ac—Nle-Asp-His-D-Phe-Arg-Trp-Lys-Gly-Pro-Val-NH$_2$ (cyclized)
Ac—Ser—Nle—Asp—His—D—Phe—Arg—Trp—Lys—Gly—Pro—Val—NH$_2$ (cyclized)

wherein M is Met, Nle or Lys; and
(b) compounds of the formula:

R$_1$—W—X—Y—Z—R$_2$ wherein
R$_1$ is Ac-Gly-, Ac-Met-Glu, Ac-Nle-Glu-, or Ac-Tyr-Glu-;
W is -His- or -D-His-;
X is -Phe-, -D-Phe-, -Tyr-, -D-Tyr-, or -(pNO$_2$)D-Phe$^7$-;
Y is -Arg- or -D-Arg-;
Z is -Trp- or -D-Trp-; and
R$_2$ is —NH$_2$; -Gly-NH$_2$; or -Gly-Lys-NH$_2$.

In another aspect, the alpha-MSH analogue may be selected from cyclic analogues which are disclosed in Australian Patent No. 618733 where an intramolecular interaction (such as a disulfide or other covalent bond) exists (1) between the amino acid residue at position 4 and an amino acid residue at position 10 or 11, and/or (2) between the amino acid residue at position 5 and the amino acid residue at position 10 or 11.

Where referred to herein, Ala=alanine, Arg=arginine, Dab=2,4-diaminobutyric acid, Dpr=2,3-diaminopropionic acid, Glu=glutamic acid, Gly=glycine, His=histidine, Lys=lysine, Met=methionine, Nle=norleucine, Orn=ornithine, Phe=phenylalanine, (pNO$_2$)Phe=paranitrophenylalanine, Plg=phenylglycine, Pro=proline, Ser=serine, Trp=tryptophan, TrpFor=N$^{1-}$formyl-tryptophan, Tyr=tyrosine, Val=valine. All peptides are written with the acyl-terminal end at the left and the amino terminal end to the right; the prefix "D" before an amino acid designates the D-isomer configuration, and unless specifically designated otherwise, all amino acids are in the L-isomer configuration.

In one aspect, the alpha-MSH analogue can be
[D-Phe$^7$]-alpha-MSH,
[Nle$^4$, D-Phe$^7$]-alpha-MSH,
[D-Ser$^1$, D-Phe$^7$]-alpha-MSH,
[D-Tyr$^2$, D-Phe$^7$]-alpha-MSH,
[D-Ser$^3$, D-Phe$^7$]-alpha-MSH,
[D-Met$^4$, D-Phe$^7$]-alpha-MSH,

[D-Glu⁵, D-Phe⁷]-alpha-MSH,
[D-His⁶, D-Phe⁷]-alpha-MSH,
[D-Phe⁷, D-Arg⁸]-alpha-MSH,
[D-Phe⁷, D-Trp⁹]-alpha-MSH,
[D-Phe⁷, D-Lys¹¹]-alpha-MSH,
[D-Phe-⁷, D-Pro¹²]-alpha-MSH,
[D-Phe⁷, D-Val¹³]-alpha-MSH,
[D-Ser¹, Nle⁴, D-Phe⁷]-alpha-MSH,
[D-Tyr², Nle⁴, D-Phe⁷]-alpha-MSH,
[D-Ser³, Nle⁴, D-Phe⁷]-alpha-MSH,
[Nle⁴, D-Glu⁵,D-Phe⁷]-alpha-MSH,
[Nle⁴, D-His⁶, D-Phe⁷]-alpha-MSH,
[Nle⁴, D-Phe⁷, D-Arg⁸]-alpha-MSH,
[Nle⁴, D-Phe⁷, D-Trp⁹]-alpha-MSH,
[Nle⁴, D-Phe⁷, D-Lys¹¹]-alpha-MSH,
[Nle⁴, D-Phe⁷·D-Pro¹²]-alpha-MSH,
[Nle⁴, D-Phe⁷, D-Val¹³]-alpha-MSH,

[Nle⁴, D-Phe⁷]-alpha-MSH$_{4-10}$,
[Nle⁴, D-Phe⁷]-alpha-MSH$_{4-11}$,
[D-Phe⁷]-alpha-MSH$_{5-11}$,
[Nle⁴, D-Tyr⁷]-alpha-MSH$_{4-11}$,
[(pNO₂)D-Phe⁷]-alpha-MSH$_{4-11}$,
[Tyr⁴, D-Phe⁷]-alpha-MSH$_{4-10}$,
[Tyr⁴, D-Phe⁷]-alpha-MSH$_{4-11}$,
[Nle⁴]-alpha-MSH$_{4-11}$,
[Nle⁴, (pNO₂)D-Phe⁷]-alpha-MSH$_{4-11}$,
[Nle⁴, D-His⁶]-alpha-MSH$_{4-11}$,
[Nle⁴, D-His⁶, D-Phe⁷]-alpha-MSH$_{4-11}$,
[Nle⁴, D-Arg⁸]-alpha-MSH$_{4-11}$,
[Nle⁴, D-Trp⁹]-alpha-MSH$_{4-11}$,
[Nle⁴, D-Phe⁷, D-Trp⁹]alpha-MSH$_{4-11}$,
[Nle⁴, D-Phe⁷]-alpha-MSH$_{4-9}$, or
[Nle⁴, D-Phe⁷, D-Trp⁹]-alpha-MSH$_{4-9}$.

In a further aspect, the alpha-MSH analogue is
[Nle⁴, D-Phe⁷]-alpha-MSH$_{4-10}$,
[Nle⁴, D-Phe⁷]-alpha-MSH$_{4-11}$,
[Nle⁴, D-Phe⁷, D-Trp⁹]-alpha-MSH$_{4-11}$, or
[Nle⁴, D-Phe⁷]-alpha-MSH$_{4-9}$.

In a particularly preferred aspect, the alpha-MSH analogue is [Nle⁴, D-Phe⁷]-alpha-MSH.

It will be appreciated that the actual preferred amounts of the alpha-MSH analogue in a specified case will vary according to the specific compounds being utilized, the particular compositions formulated, the mode of application, and the particular situs and subject being treated. Dosages for a given host can be determined using conventional considerations, e.g., by customary comparison of the differential activities of the subject compounds and of a known agent, e.g., by means of an appropriate conventional pharmacological protocol. Physicians and formulators, skilled in the art of determining doses of pharmaceutical compounds, will have no problems determining doses for inducing melanogenesis by the methods described herein. In one aspect, the alpha-MSH analogue is administered in an amount to induce melanogenesis without inducing homologous desensitization of the melanocortin-1 receptors of the subject. In another aspect, the alpha-MSH analogue is administered at a level not exceeding 10 ng/ml in the plasma of the subject for a period of at least 4 hours. In various other aspects, the alpha-MSH analogue is administered at a level not exceeding 9 ng/ml, 8 ng/ml, 7 ng/ml, 6 ng/ml, 5 ng/ml, 4 ng/ml, 3 ng/ml, 2 ng/ml, 1 ng/ml, or 0.5 ng/ml in the plasma of the subject for a period of at least 4 hours.

Any of the alpha-MSH analogues useful herein can be administered to a subject using a variety of administration or delivery techniques known in the art. It is desirable to maintain low concentrations of the alpha-MSH analogue in the plasma of the subject to induce melanogenesis in the subject. Therefore, the mode of administration will depend upon the subject to be treated and the alpha-MSH analogue selected.

In accordance with the present invention, the alpha-MSH analogue is administered in a composition or formulation which also comprises a transdermal delivery system (TDS). Preferably, the transdermal delivery system (TDS) is a system as disclosed in U.S. Pat. No. 6,444,234 (Kirby, et al.) and U.S. Pat. No. 6,787,152 (Kirby, et al.), both assigned to Transdermal Technologies, Inc., the disclosures of which are incorporated herein by reference. These disclosures describe compositions for the transdermal administration of a medicament or other active agent by topical application of the composition to the skin of humans or other animals. The disclosed methodology for formulating such compositions which provide for very rapid uptake of the active agent and transmigration into and through the skin to either fatty tissues or the vascular system, while minimizing irritation to the skin and/or immunological response, is based on a transdermal delivery system (TDS) wherein the active agent is modified to form a true solution in a complex formed from particular solvents and solvent and solute modifiers in combination with skin stabilizers. Uptake of the active agent is further facilitated and made more rapid by including forskolin or other source of cellular energy, namely induction of cAMP or cGMP. Selection of specific solvents and solvent and solute modifiers and other functional ingredients and the amounts thereof are chosen such that there is a balance between the sum of the mole-moments [(molar amount of each individual ingredient).times.(dipole moment of that ingredient)] of the delivery system and the sum of the mole-moments of the composition in which the active agent is dissolved. Preferably, the van der Waals forces of the delivery system is also similarly matched to the van der Waals forces of the total composition, namely, delivery system plus active agent.

The transdermal delivery system disclosed in U.S. Pat. Nos. 6,444,234 and 6,787,152 provides a topical formulation for the transdermal delivery of an active agent which addresses the design of the skin as a biologically responsive physical, chemical and bioelectrical barrier against the active agent(s) and solvent(s). Accordingly, solvent(s) and modifying component(s) are selected so that permanent or strong covalent bonds with the medicament or other active agent are not formed, while the complexes that are formed facilitate movement of the complex past the viable skin to its optimal targeted internal circulation system of blood, lymph or neural, or beyond these systems, wherein the complexers and modifiers are readily stripped from the active agent at the intended site of application, thereby leaving the active agent free to seek the appropriate receptors once released.

At the same time, the formulations are designed to modify the active agent and solvent(s) to minimise their reactivity and sensitizing characteristics as well as making the active agent more "slippery" thereby facilitating transmigration through the skin. By facilitating the transmigration and increasing the rate of diffusion of the active agent and other system components through the skin, the less time the formulation will have to remain in the tissues and the lower the physiological response. In part, this is accomplished by selecting solvent(s) and modifier(s) to provide a true solution, namely a solution of the various components in the solvent system on a molecular level, while at the same time forming a protective "coating" or temporary complex with the active agent to facilitate its intact transmigration through the skin.

In one broad aspect, the topical formulation for rapid transdermal delivery of an active agent through intact skin includes (1) active agent, (2) solvent system in which the active agent is soluble, (3) optionally, a substance capable of in vivo stimulation of adenosine 3',5'-cyclic monophosphate (cAMP) or cyclic guanosine 3',5'-monophosphate (cGMP), and (4) optionally, a skin stabilizer.

The substance capable of in vivo cAMP or cGMP stimulation is preferably an extract of *Coleus forskohlii*, especially a labdane diterpene, such as forskolin (colforsin) or coleonol.

The formulation may, and preferably will, also include one or more additional ingredients effective for enhancing percutaneous absorption of the active agent in its intact, bioactive form. Such additional agents include, for example, one or more of modifiers for the active agent (solute) and/or solvents such as methylsulfonylmethane, terpene compounds, skin penetration enhancers, glycerylmonolaurate, quaternium cationic surfactants, N,N-dialkyl alkanolamines such as N,N-diethylethanolamine, steroids such as dehydroepiandosterone, oily substances such as eicosapentanoic acid, and vitamins such as A, $D_3$, E, $K_1$.

The transdermal delivery system (TDS) may also include additional ingredients to provide an extended absorption curve for the topical composition, and more particularly the active agent, in order to increase absorption of the active agent following transdermal delivery through the intact skin. Such absorption modifiers may be, for example, one or more compounds selected from, for example, isopropyl myristate, benzenephenone and dimethylsulphone.

Preferably, in accordance with the present invention, the TDS comprises (a) a solvent system in which the alpha-MSH analogue (i) is soluble or at least substantially soluble, or (ii) can be made soluble or become more soluble by addition of one or more solvent and/or solute modifying agents; (b) optionally, a source of cellular activation energy; and (c) optionally, a skin stabilizer.

In one particular embodiment, this invention patent provides a topical formulation for the transdermal delivery of an active agent, wherein the active agent is an alpha-MSH analogue, and wherein the composition comprises:

(A) at least one solvent in which the active agent is soluble or which is modified to solubilize the active agent, and which has substantially the same dipole moment as that of the combination of active agent plus solvent system;

(B) at least one solvent modifier having common structural features as that of the active agent and comprising an ethylenically unsaturated polar group containing at least one functional group containing at least one heteroatom selected from the group consisting of oxygen, nitrogen and sulfur;

(C) at least one metabolizable solute modifier comprising a compound capable of forming a temporary (non-covalently bonded) complex with the active agent;

(D) at least one source of cellular activation energy; and, optionally, (E) at least one skin stabilizer for stimulating the body's repair mechanisms in response to transdermal migration of the active agent through the skin.

In a specific embodiment, the topical formulation for the transdermal delivery of an active agent, wherein the active agent is an alpha-MSH analogue, comprises:

(a) at least one non-aqueous non-toxic solvent selected from the group consisting of lower aliphatic mono- and poly-hydroxy compounds;

(b) limonene or lemon oil;

(c) methylsulfonylmethane;

(d) a solute modifier comprising at least one compound selected from the group consisting of 3,3'-thiodipropionic acid or an ester or salt thereof, an oxindole alkaloid, a polyphenolic flavonoid, a sugar adduct of a gluconuride, an isoflavone, phosphatidyl serine, phosphatidyl choline, vitamin $D_3$ and Vitamin $K_1$, (e) at least one substance which induces in situ generation of cAMP or cGMP; and (f) a skin stabilizer comprising at least one compound selected from the group consisting of an aliphatic carboxylic acid having from about 8 to about 32 carbon atoms, an ester of said aliphatic carboxylic acid with an aliphatic alcohol having from 1 to about 20 carbon atoms wherein said ester has a total of from about 9 to about 36 carbon atoms, and Vitamin $D_3$.

In accordance with a particularly preferred embodiment the component (e) is, or comprises, forskolin (colforsin).

Further details of the preferred TDS of the present invention, and methodology for formulating such systems, are disclosed in U.S. Pat. Nos. 6,444,234 and 6,787,152, the disclosures of which are incorporated herein by reference.

The amount of alpha-MSH analogue that is incorporated in the topical composition of the present invention will vary depending upon the selection of the TDS and the amount of alpha-MSH to be delivered to the subject. In one aspect, the amount of alpha-MSH analogue in the composition can be from 0.001 to 20%, 0.05 to 10% or 0.1 to 5% by weight of the composition.

Other pharmaceutically-acceptable components can be incorporated in the composition in combination with the alpha-MSH analogue. For example, the pharmaceutically-acceptable component can include, but is not limited to, a fatty acid, a sugar, a salt, a water-soluble polymer such as polyethylene glycol, a protein, polysaccharide, or carboxmethyl cellulose, a surfactant, a plasticizer, a high- or low-molecular-weight porosigen such as polymer or a salt or sugar, or a hydrophobic low-molecular-weight compound such as cholesterol or a wax.

In one aspect, any of the alpha-MSH analogues described herein can be combined with a suitable TDS, and optionally at least one pharmaceutically-acceptable carrier, to produce a pharmaceutical composition. The pharmaceutical compositions can be prepared using techniques known in the art. Pharmaceutically-acceptable carriers are known to those skilled in the art. These most typically would be standard carriers for administration to humans, including solutions such as sterile water, saline, and buffered solutions at physiological pH. Pharmaceutical compositions may also include thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like. Preparations for topical administration include aqueous or non-aqueous solutions, suspensions, and emulsions. Examples of non-aqueous carriers include water, alcoholic/aqueous solutions, emulsions or suspensions, including saline and buffered media. Preservatives and other additives may also be present such as, for example, antimicrobials, anti-oxidants, chelating agents, and the like.

Formulations for topical administration may include lotions, sprays, creams, gels, drops, ointments, suppositories, liquids and powders. Conventional pharmaceutical carriers, aqueous, powder or oily bases, thickeners and the like may be necessary or desirable. The TDS and alpha-MSH analogue can be admixed under sterile conditions with a physiologically acceptable carrier and any preservatives, buffers, propellants, or absorption enhancers as may be required or desired. Reference is made to documents cited herein, e.g., U.S. Pat. No. 5,990,091, WO 98/00166, and WO 99/60164, for the preparation of compositions for topical applications, e.g., viscous compositions that can be creams or ointments.

The methods described herein induce melanogenesis in a subject (i.e, increase melanin production from melanin-producing cells). The methods herein increase melanin production without inducing homologous desensitization of the melanocortin-1-receptors of the subject. By maintaining low concentrations of the alpha-MSH analogue in the plasma of the subject, it is possible to increase melanin production without inducing homologous desensitization of the melanocortin-1-receptors of the subject, which can prevent the occurrence of skin damage in a subject due to exposure to UV radiation. In one aspect, described herein are methods for preventing UV radiation-induced skin damage in a human subject comprising topically administering to the subject a composition comprising a TDS and an alpha-MSH analogue, wherein the alpha-MSH analogue is administered at a level to induce melanogenesis in the subject without inducing homologous desensitization of the melanocortin-1-receptors of the subject. In another aspect, described herein are methods for preventing UV radiation-induced skin damage in a human subject comprising topically administering to the subject a composition comprising a TDS and an alpha-MSH analogue, wherein the alpha-MSH analogue is administered at a level not exceeding 10 ng/ml in the plasma of the subject for a period of at least 4 hours.

EXAMPLE

The following example is put forth so as to provide those of ordinary skill in the art with a complete disclosure and description of how the compounds, compositions, and methods described and claimed herein are made and evaluated, and is intended to be purely exemplary and is not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, component mixtures, desired solvents, solvent mixtures, temperatures, pressures and other reaction ranges and conditions that can be used to optimize the product purity and yield obtained from the described process. Only reasonable and routine experimentation will be required to optimize such process conditions.

1. Introduction

These studies were conducted to assess the ability of topically applied spray-on formulations of MELANOTAN ([Nle$^4$,D-Phe-$^7$]-alpha-MSH) to penetrate the skin in hairless, pigmented guinea pigs. Blood samples were collected 1, 2, 4, 8 and 24 hours following application of the formulation for quantification of MELANOTAN ([Nle$^4$,D-Phe-$^7$]-alpha-MSH) (MT). This study was conducted with the approval of the Ethics Committee of the IMVS and the Royal Adelaide Hospital.

2. Methods 2.1. Animals

All experiments were conducted on outbred, hairless, pigmented guinea pigs specifically bred for these studies (see below). All animals were adults. Four females and eight males were used. They were housed in individual cages with sawdust for bedding, and received water and standard food ad lib. There were four groups of three animals, so that each application was applied to three animals. Two formulations were tested per experimental day, therefore six animals/day were tested over two days.

The development of the guinea pigs used in the current study was based on a breeding procedure previously reported by Bolognia et al (1990)[28]. The guinea pigs were derived from matings between outbred IMVS-coloured guinea pigs with red/brown hair, designated Hr/Hr and outbred hairless albino (Crl:IAF/HA-hairless) from a Hartley strain, designated hr/hr, obtained from Charles River Laboratories. The F, heterozygote offspring (Hr/hr) of these matings were then bred with each other or hairless albino animals avoiding sibling or cousin matings. The mating of the heterozygote animals resulting in the expected ratios of 1:2:1 for homozygous haired: heterozygote haired: homozygous hairless. Further matings were with the hairless pigmented animals (F2) with an even light brown colour. The resulting animals retain their interfollicular epidermal melanocytes and are euthymic.

2.2. Drug Formulation and Dosing

Test substance: MELANOTAN ([Nle$^4$,D-Phe-$^7$]-alpha-MSH) TDS (MT)

TDS:a standard TDS solution adjusted according to U.S. Pat. Nos. 6,444,234 and 6,787,152 (TransDermal Technologies Inc., USA).

Formulations:
  A) MT 10 mg/mL
  B) MT 10 mg/mL+2 g Isopropyl Myrisate
  C) MT 10 mg/mL+2 g Benzophenone
  E) MT 10 mg/mL +1 g Dimethylsulphone All formulations were provided in pump packs which deliver 200 µl/spray. All animals received 3 sprays, equivalent to 6 mg MT. (Storage recommendations: Below 25° C.).

2.3. Measurements

Statistical differences between the formulations over time were calculated using ANOVA with Tukey post-hoc tests (Graphpad Prism Software).

2.4. Application and Blood Collection

All blood collection was performed under Halothane anaesthesia (Zeneca Ltd., Macclesfield, UK). Blood samples (1.0 ml where possible) were taken via cardiac puncture using a 23 g needle. The samples were collected into tubes containing K$^+$EDTA and 100 µl Trasylol (10 000 KIU/ml). The blood samples were centrifuged immediately (10 000 rpm for 5 mins) and the plasma samples stored at −20° C. until analysed. The animals were administered one ml of saline sc after the 4-hour sample (animals 1-6) and after the 4- and 6-hour samples (animals 7-12) and after the 24-hour sample (all to be kept).

2.5. Treatment Protocol

The protocol was as outlined below, and the blood collection protocol as outlined in Table 1.
1) Weigh animal and record weight on clinical record sheet
2) Make sure all blood tubes labelled and have TrasyIol added (1× K⁺EDTA tube; 2× Eppendorfs-1 to centrifuge sample, 1 for analysis)
3) Fill out clinical record sheet for animal
4) Apply formulation, (all animals receiving "3 squirts", which is 600 µl, and equivalent to 6 mg of MELANOTAN ([Nle$^4$,D-Phe-$^7$]-alpha-MSH) as tested foundations are 10 mg/ml).
5) Ensure that all aerosol is applied to the back of animal and does not run off (may need to be gently rubbed in).
6) Note time of application on clinical record sheet.
7) Collect blood samples (1.0 ml where possible) as required via cardiac puncture on anaesthetised animals
8) Centrifuge bloods immediately (5 mins@10 000 rpm), remove plasma and store at −20° C. until required.

2.6. Plasma Sample Analysis

The samples were sent to Bioanalytical Sciences, Alabama, USA for MELANOTAN ([Nle$^4$,D-Phe-$^7$]-alpha-MSH) analysis by liquid chromatography with tandem mass spectrometry (LC/MS/(MS).

TABLE 1

Animal demographics and blood collections for GPT (P2)

| | Day 1 | | | | | |
|---|---|---|---|---|---|---|
| Formulation | A | | | | B | |
| Animal # | 1 | 2 | 3 | 4 | 5 | 6 |
| Sex | F | F | F | F | M | M |
| Weight (g) | 435 | 433 | 528 | 579 | 435 | 616 |
| Dose (mg/kg) | 13.8 | 13.9 | 11.4 | 10.4 | 13.8 | 9.7 |
| 60 mins | ✓ | ✓ | ✓ | ✓ | ✓ | ✓ |
| 120 mins | ✓ | ✓ | ✓ | ✓ | ✓ | ✓ |
| 240 mins | ✓ | ✓ | ✓ | ✓ | ✓ | ✓ |
| 480 mins | ✓ | ✓ | ✓ | ✓ | ✓ | ✓ |
| 1440 mins | ✓ | ✓ | ✓ | ✓ | ✓ | ✓ |
| | Day 2 | | | | | |
| Formulation | C | | | | E | |
| Animal # | 7 | 8 | 9 | 10 | 11 | 12 |
| Sex | M | M | M | M | M | M |
| Weight (g) | 627 | 659 | 661 | 652 | 715 | 545 |
| Dose (mg/kg) | 9.6 | 9.1 | 9.1 | 9.2 | 8.4 | 11.0 |
| 60 min; | ✓ | ✓ | ✓ | ✓ | ✓ | ✓ |
| 120 mins | ✓ | ✓ | ✓ | ✓ | ✓ | ✓ |
| 240 mins | ✓ | ✓ | ✓ | ✓ | ✓ | ✓ |
| 480 mins | ✓ | ✓ | ✓ | ✓ | ✓ | ✓ |
| 1440 mins | ✓ | ✓ | ✓ | ✓ | ✓ | ✓ |

3. Results

3.1. General Summary

After priming the pumps, the animals were sprayed from a distance of approximately 40 mm. This distance was ascertained as that which resulted in less aerosol loss by trialing on control guinea pigs.

A small amount of aerosol was lost to the surrounding area. The animals were sprayed in an upright position and then immediately placed on the bench. Small droplets formed with some preparations, which were gently rubbed in with a gloved finger. The formulations appeared to be well absorbed. The backs of the animals were not covered, and when dry the animals were placed in their cages containing sawdust. The formulations all had a "citrus-like" smell, with formulation C also smelling like "fly-spray".

Two of the sixty blood samples collected were mildly haemolysed. There was no indication of any procedural problems with these samples. On day 1, two of the six animals had a slight discharge from the eye (white in colour), one prior to the 2-hour sample, the other at the 6-hour sample. Both animals had clear eyes at the next sample time.

On day 1, two of the lighter animals had lost some condition and looked thin by the 24-hour sample. Additionally, one of these animals, (animal number 2, formulation A, female) was bleeding from the rectum, and appeared to have had a rectal prolapse. On day 2, another animal (formulation E, number 11, male) had also had a per rectal bleed. Another male in this group (formulation E, animal number 12) had his penis exposed (?priapism) which was covered in dried sawdust. All animals from this group were sacrificed.

The administered doses ranged from 8.4-13.9 mg/kg, with the mean dose for each group being 13.0 (formulation A), 11.3 (formulation B), 9.3 (formulation C) and 9.5 (formulation E) mg/kg.

3.2. MELANOTAN ([Nle$^4$,D-Phe-$^7$]-alpha-MSH) Concentrations in Plasma

Figure 1A:
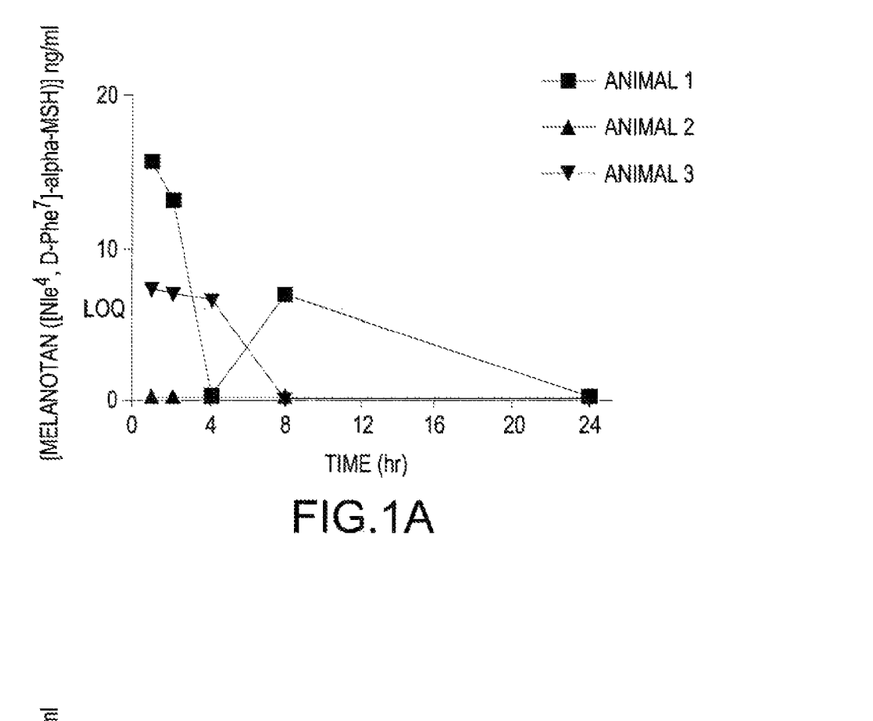
FIG. 1 shows MELANOTAN ([Nle$^4$,D-Phe-$^7$]-alpha-MSH) concentrations in plasma of guinea pigs following topical administration MELANOTAN ([Nle$^4$,D-Phe$^7$]-alpha-MSH)/TDS (MT) formulations A, B, C and E.
Figure 1B:
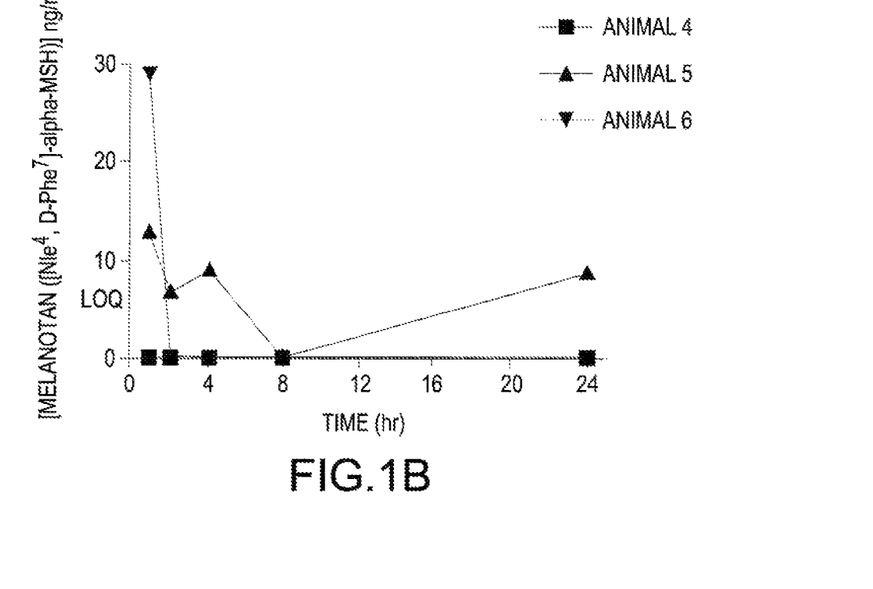
Figure 1C:
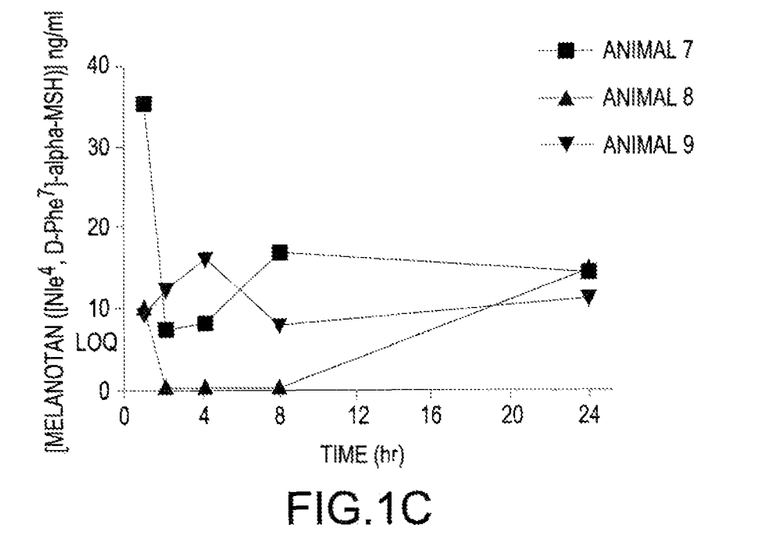
Figure 1D:
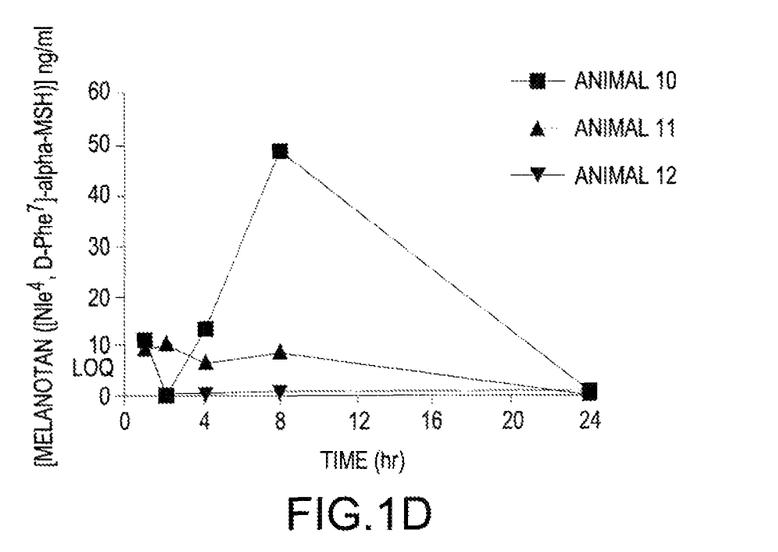
Figure 2A:
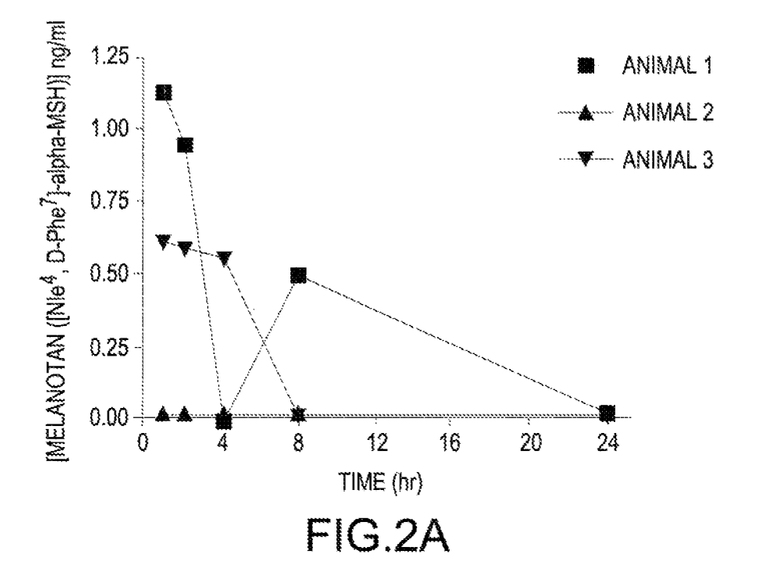
FIG. 2 shows dose-corrected MELANOTAN ([Nle$^4$,D-Phe-$^7$]-alpha-MSH) concentrations in plasma of guinea pigs following topical administration of MT formulations A, B, C and E.
Figure 2B:
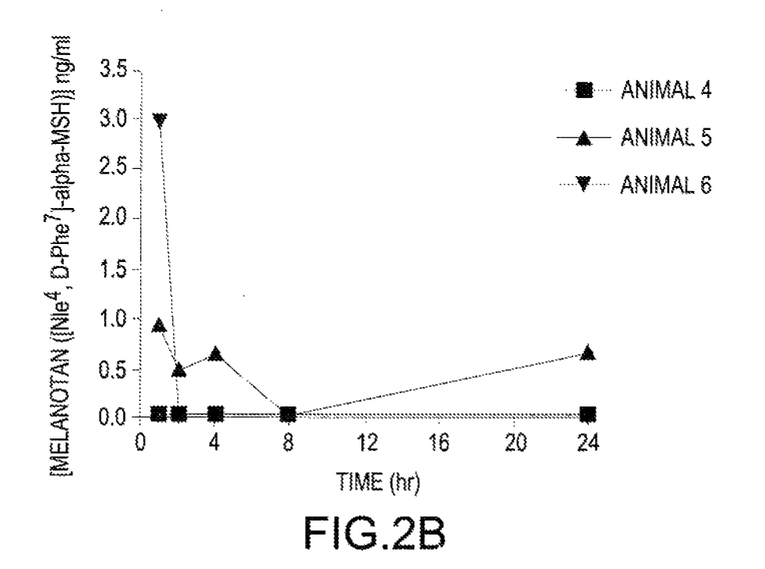
Figure 2C:
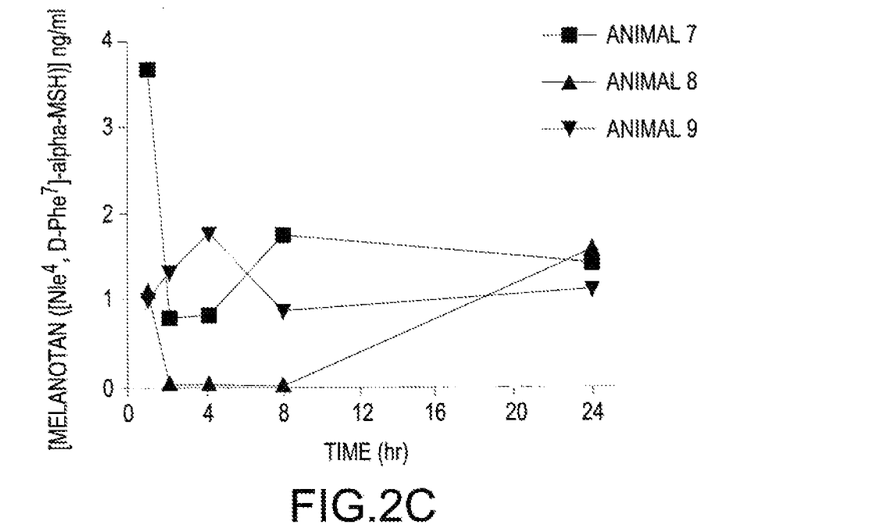
Figure 2D:
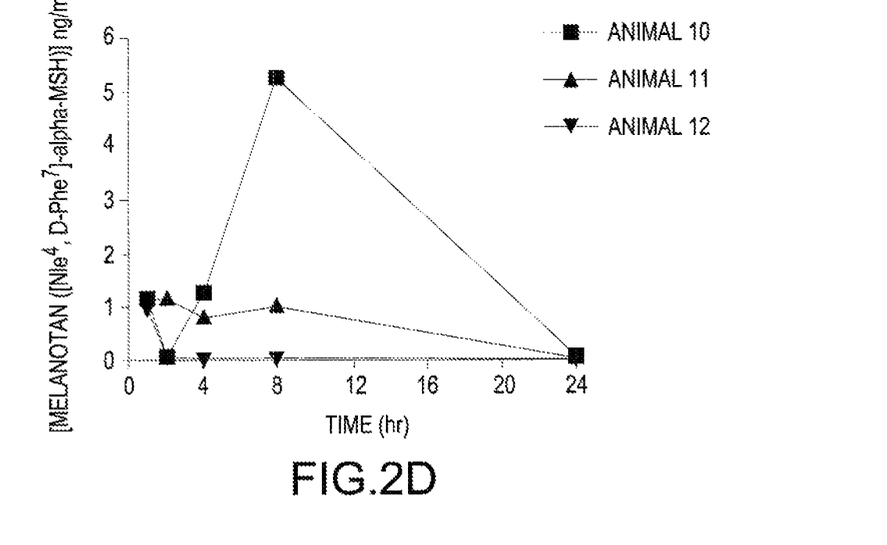
Figure 3:
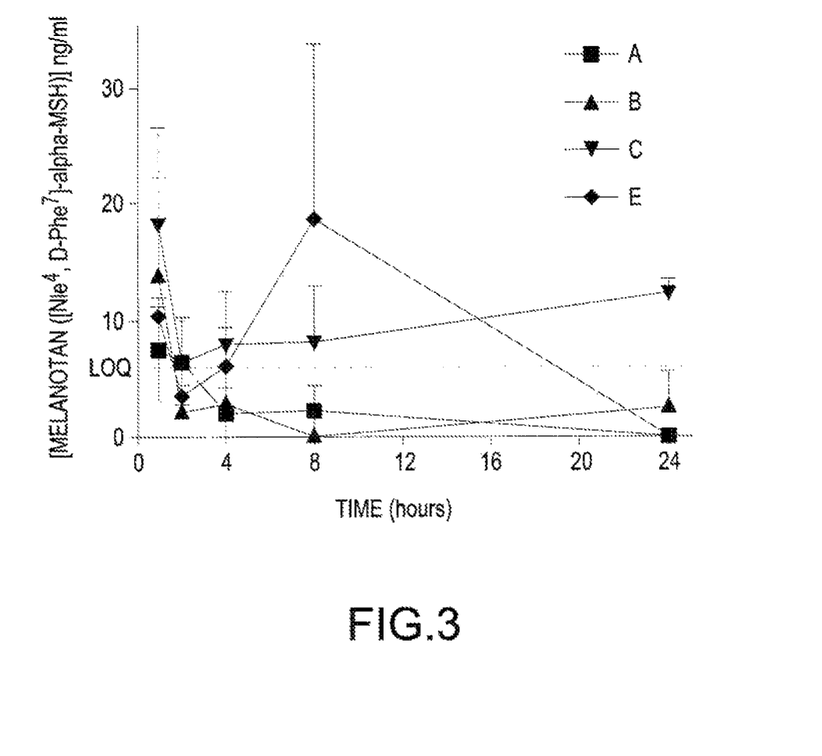
FIG. 3 shows mean plasma MELANOTAN ([Nle$^4$,D-Phe-$^7$]-alpha-MSH) concentrations MT formulations A, B, C and E.
Figure 4:
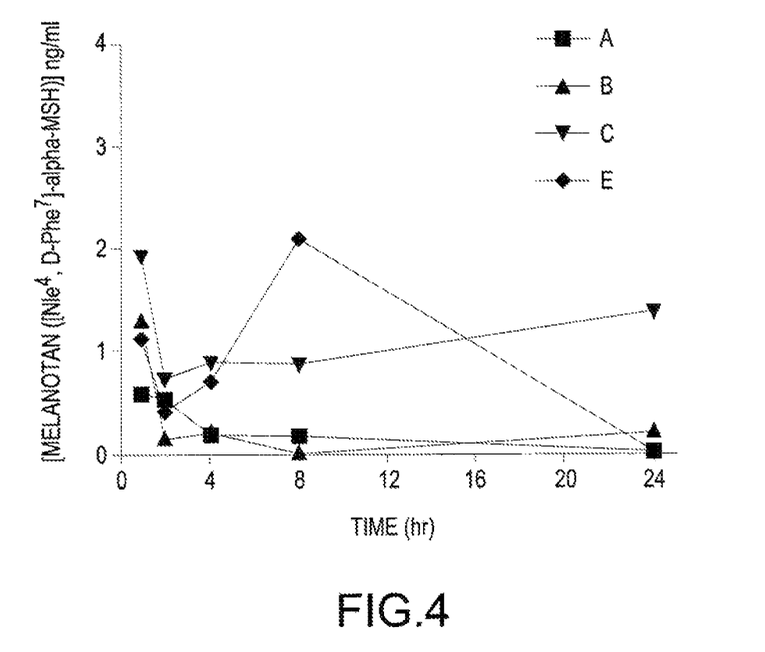
FIG. 4 shows mean dose-corrected plasma. MELANOTAN ([Nle$^4$,D-Phe-$^7$]-alpha-MSH) concentrations for MT formulations A, B. C and E.

Table 2. shows the plasma concentrations obtained for each sample. As can be seen from the results obtained, there were a number of animals for which the MELANOTAN ([Nle$^4$,D-Phe-$^7$]-alpha-MSH) plasma levels were undetectable. The results for each group individually are shown in FIG. 1(*a-d*), with the corresponding results shown for the levels obtained corrected for the mg/kg dose administered depicted in FIG. 2(*a-d*). The result for animal 1 (Formulation A) at the four-hour time point is not included in any calculation or graph. This is a spuriously high result, but as the sample volumes were short, there was not enough to repeat the sample. The mean (+SEM) plasma concentrations of MELANOTAN ([Nle$^4$, D-Phe-$^7$]-alpha-MSH) are shown in FIG. 3, with the dose-corrected results shown in FIG. 4 (the error bars have been removed for clarity). There are no significant differences between any of the formulations in the dose-corrected data.

TABLE 2

MELANOTAN ([Nle$^4$, D-Phe$^7$]-alpha-MSH) obtained by concentrations (nglmL) LCIMMSIMMS

| Formulation & Dose (mg/kg) | Sample Name | MT (ng/mL) |
|---|---|---|
| A<br>13.8 | Subject 01 - 1 hr | 15.6 |
| | Subject 01 - 2 hr | 13.0 |
| | Subject 01 - 4 hr | 2978 |
| | Subject 01 - 8 hr | 6.8 |
| | Subject 01-24 hr | 0.0 |
| A<br>13.9 | Subject 02 - 1 hr | 0.0 |
| | Subject 02 - 2 hr | 0.0 |
| | Subject 02 - 4 hr | 0.0 |
| | Subject 02 - 8 hr | 0.0 |
| | Subject 02-24 hr | 0.0 |
| A<br>11.4 | Subject 03 - 1 hr | 7.0 |
| | Subject 03 - 2 hr | 6.7 |
| | Subject 03 - 4 hr | 6.4 |
| | Subject 03 - 8 hr | 0.0 |
| | Subject 03-24 hr | 0.0 |
| B<br>*<br>10.4 | Subject 04 - 1 hr | 0.0 |
| | Subject 04 - 2 hr | 0.0 |
| | Subject 04 - 4 hr | 0.0 |
| | Subject 04 - 8 hr | 0.0 |
| | Subject 04-24 hr | 0.0 |
| B<br>13.8 | Subject 05 - 1 hr | 13.0 |
| | Subject 05 - 2 hr | 6.7 |
| | Subject 05 - 4 hr | 9.0 |
| | Subject 05 - 8 hr | 0.0 |
| | Subject 05-24 hr | 8.4 |
| B | Subject 06 - 1 hr | 29.0 |

TABLE 2-continued

MELANOTAN ([Nle⁴, D-Phe⁷]-alpha-MSH) obtained by concentrations (ng|mL) LCIMMSIMMS

| Formulation & Dose (mg/kg) | Sample Name | MT (ng/mL) |
|---|---|---|
| 9.7 | Subject 06 - 2 hr | 0.0 |
|  | Subject 06 - 4 hr | 0.0 |
|  | Subject 06 - 8 hr | 0.000 |
|  | Subject 06-24 hr | 0.000 |
| C | Subject 07 - 1 hr | 35.20 |
| 9.6 | Subject 07 - 2 hr | 7.6 |
|  | Subject 07 - 4 hr | 8 |
|  | Subject 07 - 8 hr | 16.6 |
|  | Subject 07-24 hr | 13.4 |
| C | Subject 08 - 1 hr | 10.3 |
| 9.1 | Subject 08 - 2 hr | 0 |
|  | Subject 08 - 4 hr | 0 |
|  | Subject 08 - 8 hr | 0 |
|  | Subject 08-24 hr | 14.1 |
| C | Subject 09 - 1 hr | 8.8 |
| 9.1 | Subject 09 - 2 hr | 12 |
|  | Subject 09 - 4 hr | 15.9 |
|  | Subject 09 - 8 hr | 7.8 |
|  | Subject 09-24 hr | 10.1 |
| E | Subject 10 - 1 hr | 11.3 |
| 9.2 | Subject 10 - 2 hr | 0.0 |
|  | Subject 10 - 4 hr | 11.8 |
|  | Subject 10 - 8 hr | 48.4 |
|  | Subject 10-24 hr | 0.0 |
| E | Subject 11 - 1 hr | 9.2 |
| 8.4 | Subject 11 - 2 hr | 10.0 |
|  | Subject 11 - 4 hr | 6.6 |
|  | Subject 11 - 8 hr | 8.2 |
|  | Subject 11- 24 hr | 0.0 |
| E | Subject 12 - 1 hr | 11.3 |
| 11.0 | Subject 12 - 2 hr | 0 |
|  | Subject 12 - 4 hr | 0 |
|  | Subject 12 - 8 hr | 0 |
|  | Subject 12-24 hr | 0 |

\* Samples mildly haemolysed.

4. Summary and Conclusions

All formulations were very simple to apply with little lost to the surrounding area. Additionally, they all appeared to penetrate the skin quickly and easily. It is unknown why one animal receiving formulation A and one receiving formulation E should have been bleeding from the rectum. This has not been noted before in previous studies where animals were bled this frequently, so it is thought not to be stress-related. The female that received formulation A was examined post-mortem, but there was no evidence of any bleeding higher in the gastrointestinal tract, and no obvious cause.

The experimental numbers tested for each group were low (n=3), and there was a large interindividual variation in the plasma MELANOTAN ([Nle⁴, D-Phe⁷]-alpha-MSH) concentrations obtained within the groups. As the expected plasma concentrations were between 1 and 10 ng/ml, the limit of quantification of the assay needs to be lower than 6 ng/ml to detect these levels in plasma.

References

1. Hadley M E. The melanotropic hormones. In: Brake D, editor. Endocrinology. 4th Edition, Simon & Schuster; (1982). p. 153-76.
2. Thody A J, et al. Pheomelanin as well as eumelanin are present in human epidermis. *J. Invest Dermatol* (1991); 97:340-44.
3. Valverde P, et al. Variants of the melanocyte-stimulating hormone receptor gene are associated with red hair and fair skin in humans. *Nature Genet* (1995);11:328-30.
4. Box N F. et al. Melanocortin-1 receptor genotype is a risk factor for basal and squamous cell carcinoma. *J Invest Derm* (2001); 116:224-29.
5. Palmer J S. et al. Melanocortin-1 receptor polymorphisms and risk of melanoma: is the association explained solely by pigmentation phenotype? *Am J Hum Genet* (2000); 66:176-86.
6. Levine N, et al. Induction of skin tanning by subcutaneous administration of a potent synthetic melanotropin. *JAMA* (1991); 266:2730-736.
7. Sawyer T K, et al. [Nle⁴-D-Phe⁷]-α-melanocyte stimulating hormones: a highly potent α-melanotropin with ultralong biological activity. *Proc Natl Acad Sci USA* (1980); 77:5754-8.
8. Dorr R T, et al. Increased eumelanin expression and tanning is induced by a superpotent melanotropin [Nle⁴D-Phe⁷]-α-MSH in humans. *Photochem Photobiol* (2000); 72:526-32.
9. Lipton J M, et al. Antiinflammatory effects of the neuropeptide alpha-MSH in acute, chronic and systemic inflammation. *Ann NY Acad Sci* (1994); 741:137-48.
10. Ceriani G, et al. The neuropeptide alpha-melanocyte-stimulating hormone inhibits experimental arthritis in rats. *Neuroimmunomodulation* (1994); 1:28-32.
11. Chiao H S, et al. α-melanocyte-stimulating hormone reduces endotoxin-induced liver inflammation. *J Clin Invest* (1996); 97:2038-44.
12. Levine N, et al. Effects of a potent synthetic melanotropin, Nle⁴-D-Phe⁷-α-MSH (Melanotan-1) on tanning: a dose-ranging study. *J Derm Treat* (1999); 19:127-32.
13. Bhardwaj, R, et al. In vitro characterisation and in vivo release profile of a poly(D,L-lactide-co-glycolide)-based implant delivery system for the α-MSH analog, Melanotan-1. *Int. J. Pharm.* (1998), 170:109-117.
14. Bhardwaj R, et al., Pharmacologic response of a controlled-release PLGA formulation for the alpha-melanocyte stimulating hormone analog, Melanotan-1. *Pharmaceutical Research* (2000); 17:583-9.
15. Bhardwaj, R, et al. Controlled-release delivery system for the α-MSH analog, Melanotan-1 using Polyoxamer 407. *J Pharm. Sci.* (1996) 15:915-919.
16. Fitzpatrick T B. The validity and practicality of sun-reactive skin types I through VI. *Arch. Dermatol.* (1988) 124: 869-871.
17. Graham I H. Precancerous lesions of the skin. *Primary Care* (1975) 2: 699-766.
18. Stenback F. Life history and histopathology of ultraviolet light-induced skin tumours. *National Cancer Institute Monograph* (1978) 50: 57-70.
19. De L. Castrucci A M et al. Synthesis and studies of superpotent melanotropins resistant to enzyme degradation. *Comp. Biochem. Physiol.* (1984) 78B: 519-524.
20. Hadley M E et al. [Nle⁴-D-Phe⁷]-α-MSH: a superpotent melanotropin that "irreversibly" activates melanoma tyrosinase. *Endocr. Res.* (1985) 11:157-170.
21. Dawson B V et al. Administration of melanotropic peptides during gestation in the rodent. *Toxicol.* (1993) 77: 91-101.
22. Dorr R T et al. Toxicologic studies of a superpotent α-melanotropin, [Nle⁴-D-Phe⁷]-α-MSH. *Invest. New Drugs* (1988) 6: 251-258.
23. Dorr R T. and Dawson B V. Toxicology report: Results of a 30 day study of MELANOTAN-I given subcutaneously to adult rats. *University of Arizona internal report.* (1988).
24. Dorr R T. Thirty day Toxicology study of Melanotan-I [Nle⁴-D-Phe⁷]-α-MSH in miniature Yucatan swine. *University of Arizona, Laboratory Booklet—Chris Brooks* (1993).

25. Levine N et al. Effects of a potent synthetic melanotropin, Nle[4]-D-Phe[7]-α-MSH (Melanotan-I) on tanning: Dose ranging study. *J. Dermatol. Treat.* (1999) 10 (2): 127-132.
26. Dorr R T et al. Increased eumelanin expression and tanning is induced by a superpotent melanotropin [Nle[4]-D-Phe[7]]-α-MSH in humans. *Photochem & Photobiol.* (2000).
27. Evans A et al. A Randomised, Placebo-Controlled, Double-Blind Study to Assess the Pharmacokinetics and Tanning Effect of Melanotan in Healthy Adult Subjects *Study Report August* (2000).
28. Bolognia, et al. Hairless pigmented guinea pigs: a new model for the study of mammalian pigmentation. *Pigment Cell Res.* (1990) 3(3):150-6.

The invention claimed is:

1. A topical composition for the transdermal delivery of an active agent, wherein the active agent is [Nle[4], D-Phe[7]]-alpha MSH, and wherein the composition comprises:
   (a) at least one non-aqueous non-toxic solvent selected from the group consisting of lower aliphatic mono- and poly-hydroxy compounds;
   (b) limonene, lemon oil, or a mixture of limonene and lemon oil;
   (c) methylsulfonylmethane;
   (d) a solute modifier comprising at least one compound selected from the group consisting of 3,3'-thiodipropionic acid or an ester or salt thereof, an oxindole alkaloid, a polyphenolic flavonoid, a sugar adduct of a gluconuride, an isoflavone, phosphatidyl serine, phosphatidyl choline, Vitamin $D_3$ and Vitamin $K_1$;
   (e) at least one substance which induces in situ generation of cAMP or cGMP, wherein the at least one substance comprises forskolin; and
   (f) a skin stabilizer comprising at least one compound selected from the group consisting of an aliphatic carboxylic acid having from about 8 to about 32 carbon atoms, an ester of said aliphatic carboxylic acid with an aliphatic alcohol having from to about 20 carbon atoms wherein said ester has a total of from about 9 to about 36 carbon atoms, and Vitamin $D_3$, and
   wherein the composition further comprises one or more absorption modifiers selected from isopropyl myristate and benzophenone.

2. The composition of claim 1, wherein the amount of alpha-MSH analogue in the formulation is 0.001 to 20% by weight.

3. The composition of claim 2, wherein the amount of alpha-MSH analogue in the formulation is 0.05 to 10% by weight.

4. A method for inducing melanogenesis in a subject comprising topically administering to the subject a composition of claim 1.

5. The method of claim 4, comprising administering said composition to provide alpha-MSH analogue in an effective amount and time to induce melanogenesis by the melanocytes in epidermal tissue of the subject without inducing homologous desensitization of the melanocortin-1 receptors of the subject.

6. The method of claim 4, comprising administering alpha-MSH analogue at a level not exceeding 10 ng/ml in the plasma of the subject for a period of at least 4 hours.

* * * * *